Figure 1:
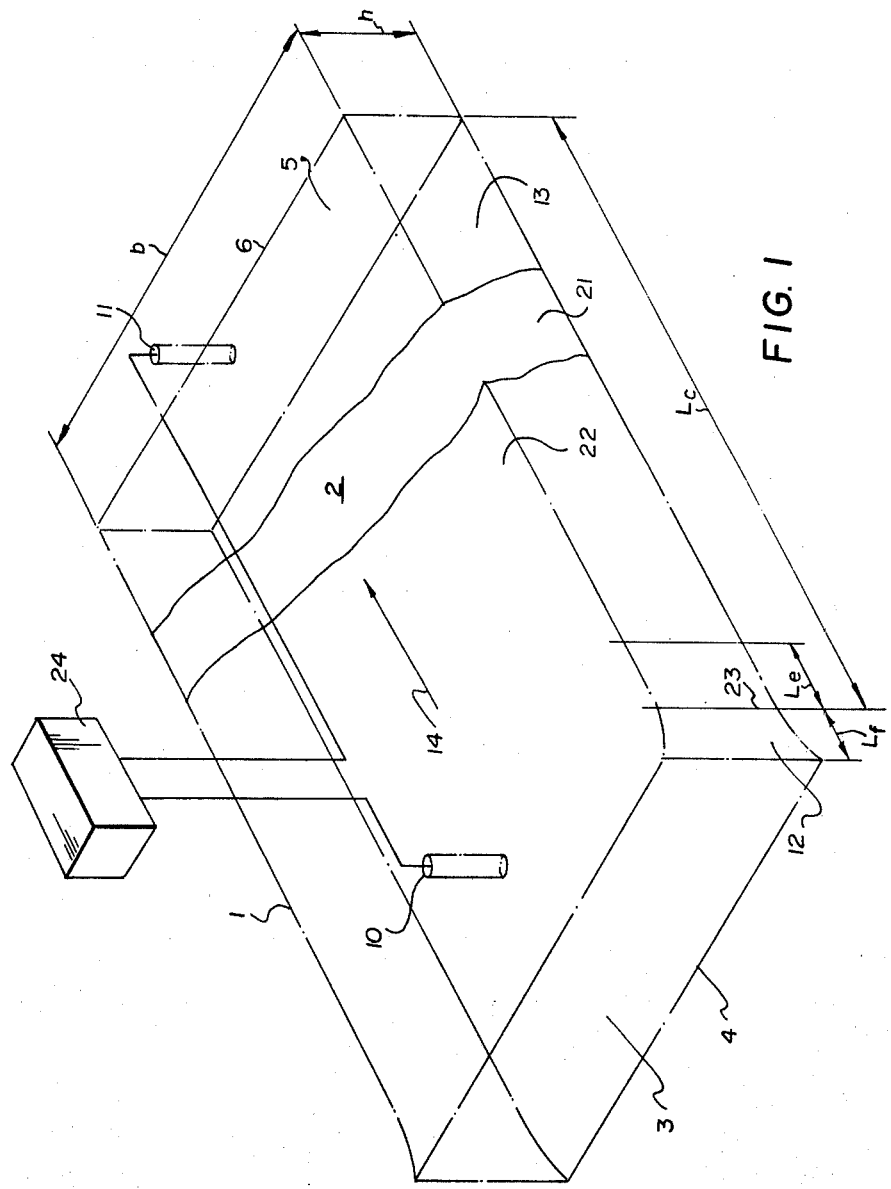

United States Patent [19]

Tucker et al.

[11] 4,118,973

[45] Oct. 10, 1978

[54] APPARATUS FOR MEASURING THE FLOW RATE AND/OR VISCOSITY OF A FLUID

[75] Inventors: Helen G. Tucker, Orleans; John W. Tanney; William F. Hayes, both of Ottawa, all of Canada

[73] Assignee: Canadian Patents & Development Limited, Ottawa, Canada

[21] Appl. No.: 831,087

[22] Filed: Sep. 6, 1977

[30] Foreign Application Priority Data

Sep. 6, 1976 [GB] United Kingdom ............... 36828/76

[51] Int. Cl.² ....................... G01N 11/04; G01F 1/36
[52] U.S. Cl. ........................................ 73/55; 73/205 L
[58] Field of Search ........................... 73/55, 56, 205 L

[56] References Cited

U.S. PATENT DOCUMENTS

| | | | |
|---|---|---|---|
| 2,212,186 | 8/1940 | Ricardo et al. | 73/205 L |
| 3,071,001 | 1/1963 | Goldsmith | 73/205 L |
| 3,071,160 | 1/1963 | Weichbrod | 73/205 L |
| 3,220,256 | 11/1965 | Weichbrod | 73/205 L X |
| 3,349,619 | 10/1967 | Millar | 73/205 L |
| 3,677,069 | 7/1972 | Rubin et al. | 73/56 |
| 3,838,598 | 10/1974 | Tompkins | 73/205 L |
| 3,952,577 | 4/1976 | Hayes et al. | 73/55 |

*Primary Examiner*—Richard C. Queisser
*Assistant Examiner*—Joseph W. Roskos
*Attorney, Agent, or Firm*—Francis W. Lemon

[57] ABSTRACT

An apparatus for measuring the flow rate and/or viscous characteristics of a fluid comprises a casing, having a fluid passage which is elongated in cross-section with two parallel, opposed sides and has a flared entry portion leading to a portion of constant cross-section. Formulae are given, using substantially pure water as a standard, from which a suitable geometry for the flared entry portion can be deduced. Fluid pressure detectors are provided for detecting a fluid pressure differential in the fluid passage such that the fluid characteristic to be measured may be deduced from the pressure differential when laminar flow is maintained in the passage. When laminar flow is maintained the apparatus is capable of measuring a wide range of flow rates and/or viscosities of an extensive variety of fluids in a consistent and deducible manner with minimal pressure loss.

11 Claims, 42 Drawing Figures

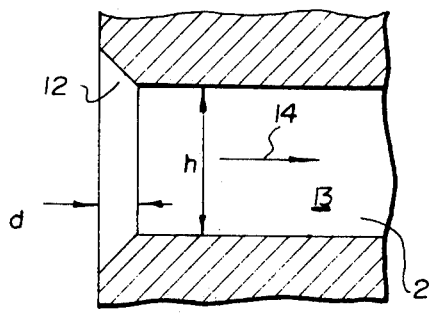
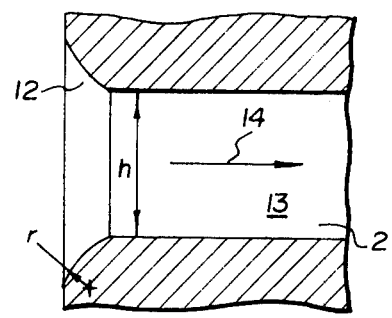
FIG. 11 　　　　　FIG. 12
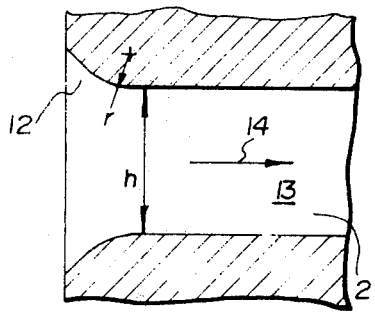
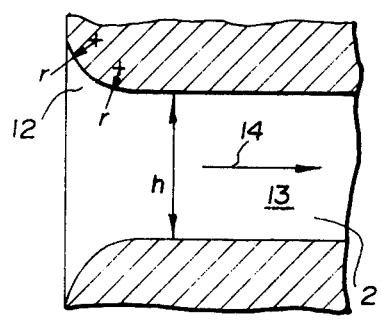
FIG. 13 　　　　　FIG. 14
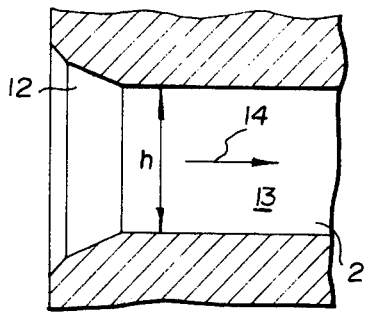
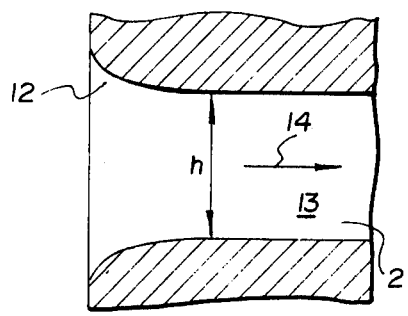
FIG. 15 　　　　　FIG. 16

APPARATUS FOR MEASURING THE FLOW RATE AND/OR VISCOSITY OF A FLUID

This invention relates to apparatus for measuring the flow rate and/or the viscosity of a fluid.

More particularly, in some embodiments of the present invention there is provided an apparatus for measuring the flow rate of fluid wherein the fluid flow through the apparatus is laminar and wherein the excess pressure loss across the apparatus relative to the useful output signal indicative of flow rate is minimized in contrast with known apparatus. Further, according to some embodiments of the present invention there is provided an apparatus for measuring the viscosity of Newtonian fluids, or for the measurement of viscosity of non-Newtonian fluids, at a single shear rate with a fixed flow of fluid through the apparatus.

In other embodiments, the present invention provides an apparatus for measuring the flow rate of a fluid wherein a reduction of pressure loss in the fluid is achieved, relative to known apparatus, when entering a constant cross-section laminar flow portion of a fluid passage such known apparatus is described for example, by Ricardo in U.S. Pat. No. 2,212,186, Goldsmith in U.S. Pat. No. 3,071,001, Weichbrod in U.S. Pat. Nos. 3,071,160 and 3,220,256, Millar in U.S. Pat. No. 3,349,619, Palmer in U.K. Pat. No. 767,047 and Brunswick Corp. in U.K. Pat. No. 1,306,161.

In this specification, a fluid may consist of a gas, a liquid, a liquid containing a dissolved gas or dissolved gases, a mixture of gas and liquid, gas and suspended solids, liquid and suspended solids, where it can be assumed that such mixtures have the properties of either a compressible or an incompressible fluid.

Further, in this specification, fluids considered as being Newtonian are defined as those exhibiting a direct proportionality between shear stress and shear rate in laminar flow at a fixed fluid temperature and pressure.

Further, in this specification, laminar flow is defined as a fluid flow having insignificant random or irregular flow velocity components in contrast with turbulent flow where such irregularities are significant.

The measurement of fluid flow rate is a long standing problem which has been approached with a wide variety of techniques, each of which exhibits particular advantages and deficiencies relative to particular applications.

The principles relative to measuring fluid flow rates may be classified into five general groupings:

Heat transfer rate to or from fluids as exemplified by hot wire anemometers or similar devices.

Transport time of extraneous media suspended in or driven by the fluid as exemplified by the time displacement relationship of ion clouds, solid bodies, bubbles, etc.; transport time of disturbances within the fluid itself as exemplified by the time displacement correlation of inherent or induced fluid turbulence noise spectra.

Fluid momentum detection as exemplified by pitot tubes or venturi meters; fluid momentum utilization as exemplified by cup anemometers or tubine meters; and fluid momentum interaction as exemplified by fluid jet velocity sensors.

Fluid disturbance detection as exemplified by vortex shedding flow-meters and vortex generation detecting swirlmeters.

Fluid viscosity induced phenomena as exemplified by laminar flow pressure drop devices.

Fluid viscosity induced pressure drop apparatus for fluid flow rate measurement is well known as exemplified by the above noted references, wherein the pressure loss due to entrance effects into the laminar flow passages are noted as being proportional to the square of the measured flow rate as is described in standard fluid dynamics texts.

Many types of apparatus are available for measuring the viscosity of fluids (Reference, Viscosity and Flow Measurement-A-Laboratory Handbook of Rheology: Van Wazer, Lyons, Kim, Colwell: Interscience, New York, 1963). Known types of apparatus presently used for the precise measurement of fluid viscosity may be classified into three general groupings:

capillary-tube type viscometers where the fluid viscosity is directly related to the frictional pressure drop and laminar flow rate through a long smooth tube.

rotary type viscometers where the fluid is sheared within an annulus between two concentric cylinders, one of which is rotating, the fluid viscosity being directly related to the reaction torque and speed of the cylinders.

falling-sphere type viscometers where the fluid viscosity is directly related to the velocity of a sphere free falling through the fluid as dependent on gravity.

These known types of apparatus, with the exception of the capillary tube viscometer, are not generally suitable, in their basic configurations, for continuously measuring the viscosity of a flowing fluid. In contrast with known capillary tube viscometers which are difficult to clean and are not capable of adjustment the present invention provides an apparatus, which can carry out the same function, but with a lower overall pressure drop across the apparatus and additionally can be dismantled for cleaning, and which may be readily adjusted by the replacement of a profiled plate or shim member.

It is one object of the present invention to provide an apparatus capable of measuring a wide range of flow rates and/or viscosities of an extensive variety of fluids such that the output differential pressure of the said apparatus can be continuously related to the said fluid characteristics in a consistent and deducible manner while minimizing the pressure loss across the entire apparatus relative to the useful output pressure which is responsive to the fluid characteristic which is being measured, in contrast with the disadvantages of many known types of apparatus for measuring fluid flow rate and/or viscosity.

This invention differs from known apparatus, as exemplified by the above noted references, in that the geometry of the entry portion into a substantially constant cross-section passage or passages is defined in terms of a "figure or merit" by means of a test which may be readily conducted by those skilled in the art and where the upstream pressure measuring location in the fluid passage may be defined in terms of another "figure of merit" as will become apparent in the following description of the present invention.

According to the present invention there is provided an apparatus for measuring the flow rate and/or viscosity of a fluid comprising:

a. a casing having a fluid passage, which is elongated in cross-section normal to the mean direction for fluid flow therein with two parallel, opposed major boundary surface portions which are parallel in a plane normal to the mean direction for fluid flow therebetween, the fluid passage comprising a flared entry portion and a portion having, in the mean direction for fluid flow therein, continuous boundary surface and a substantially constant cross-section, the flared entry portion being flared to decrease in width, without increasing in breadth, in the mean direction for fluid flow therein and forming an unobstructed flow path to the portion having, in the mean direction for fluid flow therein, a continuous boundary surface and a substantially constant cross-section, a fluid inlet to the casing and forming a substantially unobstructed flow path for fluid to the whole of an inlet area to the flared entry portion of the fluid passage, said inlet area being normal to the mean direction for flow of fluid at an inlet end of the flared entry portion, and fluid outlet from the casing and forming a substantially unobstructed flow path for fluid from the whole area of an outlet end of the fluid passage said outlet area being normal to the mean direction for flow of fluid at the outlet end of the fluid passage, and wherein b. the portion of the fluid passage having continuous boundary surface and a substantially constant cross-section in the mean direction for fluid flow therein has a magnitude of mean breadth which is at least as large as that given by a mean breadth to mean width ratio of 1.5 to 1, and an area in any plane normal to the mean direction for fluid flow therein which does not vary more than in the region of 2% from the mean area calculated in this manner for substantially the whole length of the said portion having continuous boundary surface and a substantially constant cross-section, and wherein c. the geometry of the flared entry portion of the fluid passage is such that, with laminar flow being maintained in the whole of the fluid passage, using substantially pure water at 70° F. as a standard, the flared entry portion has a "figure of merit", M which is calculated using consistent units from the relationship:

$$M = 1 - \frac{K_2 G_2}{\Delta E_2}$$

where, $G_2$ = the mass flow rate of the substantially pure water through the fluid passage when the Reynolds number, $R_e$, is at least 2000 in the portion of the fluid passage having continuous boundary surface and a substantially constant cross-section in the mean direction for fluid flow therein, and the Reynolds number, $R_e$, in the portion of the fluid passage having continuous boundary surface and a substantially constant cross-section is defined in consistent units by the relationship:

$$R_e = \frac{h \bar{U} \rho}{\mu}, \text{ where}$$

$h$ = the width separating the parallel opposed major boundary surface portions, of the portion of the fluid passage having continuous boundary surface and a substantially constant cross-section in the mean direction for fluid flow therein, $\bar{U}$ = the mean velocity of the substantially pure water through the portion of the fluid passage having continuous boundary surface and a substantially constant cross-section in the mean direction for fluid flow therein, $\rho$ = the density of the substantially pure water, $\mu$ = the absolute viscosity of the substantially pure water, $\Delta E_2$ = a static pressure differential between the substantially pure water at or upstream of the fluid inlet to the casing and the substantially pure water within the fluid passage at a position within the portion having continuous boundary surface and a substantially constant cross-section in the mean direction for fluid flow therein and where the flow rate is $G_2$ as previously defined immediately above and which is downstream of an outlet end of the flared entry portion by at least an amount $L_e$ and is determined in consistent units by the relationship:

$L_e = 0.04 R_e h$ when the Reynolds number, $R_e$, is that where the flow rate is $G_2$ as previously defined immediately above in the portion of the fluid passage having continuous boundary surface and a substantially constant cross-section in the mean direction for fluid flow therein, $K_2$ is a constant and is defined in consistent units by, $$K_2 = \frac{\Delta E_1 - \Delta E_2 \left(\frac{G_1}{G_2}\right)^2}{G_1 - \frac{(G_1)^2}{G_2}}, \text{ where}$$

$G_1$ = the mass flow rate of the substantially pure water through the fluid passage when the Reynolds number $R_e$, is less than $G_2$ and is at least 1000 in the portion of the fluid passage having continuous boundary surface and a substantially constant cross-section in the mean direction for fluid flow therein, and $\Delta E_1$ = a static pressure differential between the substantially pure water at or upstream of the fluid inlet to the casing and the substantially pure water within the fluid passage at a position within the portion having continuous boundary surface and a substantially constant cross-section in the mean direction for fluid flow therein and where the flow rate is $G_1$ as previously defined immediately above and which is downstream of the outlet end of the flared entry portion by at least an amount $L_e$ as previously defined, and where the flared entry portion "figure of merit", M, is within the limits determined by the relationship in consistent units:

$$M < 1.36 \frac{h}{d_h}, \text{ where}$$

$d_h$ = the hydraulic diameter of the portion of the fluid passage having continuous boundary surface and a substantially constant cross-section in the mean direction for the flow of fluid therein, and is defined in consistent units by, $$d_h = \frac{4A}{C}, \text{ where}$$

$A$ = cross-sectional area of the portion of the fluid passage having continuous boundary surface, and a substantially constant cross-section, normal to the mean direction for fluid flow therein, $C$ = wetted perimeter of the portion of the fluid passage having continuous boundary surface, and a substantially constant cross-section, in a plane normal to the mean direction for fluid flow therein, and where $h$ is as previously defined, and d. fluid pressure detecting means in the casing for detecting a fluid pressure differential in the fluid passage, between spaced positions in the mean direction for fluid flow therein, at least one of the positions being in the portion having continuous boundary surface and a substantially constant cross-section, whereby e. the or each fluid characteristic to be measured is related to the pressure differential indicated by the fluid pressure detecting means and is deducible therefrom in a consistent manner for any given fluid when laminar flow is maintained in the whole of the fluid passage.

Further, according to the present invention there is provided an apparatus for measuring the flow rate and-/or the viscous characteristics of a fluid, comprising:

a. a casing having a plurality of substantially identical fluid passages, which are elongated in cross-section normal to the mean direction for fluid flow therein with each passage having two parallel, opposed major boundary surface portions, which are parallel in a plane normal to the mean direction for fluid flow therethrough, each fluid passage comprising a flared entry portion and a portion having, in the mean direction for fluid flow therein, continuous boundary surface and a substantially constant cross-section, the flared entry portion of each passage being flared to decrease in width, without increasing in breadth, in the mean direction for fluid flow therein and forming an unobstructed flow path to the portion, having in the mean direction for fluid flow therein, continuous boundary surface and a substantially constant cross-section, a fluid inlet to the casing forming a substantially unobstructed flow path for fluid to the whole of an inlet area to the flared entry portion of each fluid passage, for each fluid passage said inlet area being normal to the mean direction for flow of fluid at an inlet end of the flared entry portion, a fluid outlet from the casing forming a substantially unobstructed flow path for fluid from the whole area of an outlet end of each fluid passage, for each fluid passage, said outlet area being normal to the mean direction for flow of fluid at the outlet end of that fluid passage, and wherein b. the portion of each fluid passage having continuous boundary surface and a substantially constant cross-section in the mean direction for fluid flow therein has a magnitude of mean breadth which is at least as large as that given by a mean breadth to mean width ratio of 1.5 to 1, and an area in any plane normal to the mean direction for fluid flow therein which does not vary more than in the region of 2% from the mean area calculated in this manner for the whole length of the said portion of that fluid passage having continuous boundary surface and a substantially constant cross-section, and wherein c. the geometry of the flared entry portion of each fluid passage is such that, with laminar flow being maintained in the whole of each fluid passage, using substantially pure water at 70° F. as a standard, the flared entry portion of each fluid passage has a "figure of merit", M which is substantially the same for each fluid passage and which is calculated using consistent units from the relationship:

$$M = 1 - \frac{K_2 G_2}{\Delta E_2}$$

where, $G_2$ = the mass flow rate of the substantially pure water through each of the fluid passages when the Reynolds number $R_e$, is at least 2000 in the portion of each fluid passage having continuous boundary surface and a substantially constant cross-section in the mean direction for fluid flow therein, and the Reynolds number, $R_e$, in the portion of each of the fluid passages having continuous boundary surface and a substantially constant cross-section is defined in consistent units by the relationship:

$$R_e = \frac{h \bar{U} \rho}{\mu}, \text{ where}$$

$h$ = the width separating the parallel opposed major boundary surface portions, of the portion of each fluid passage having continuous boundary surface and a substantially constant cross-section in the mean direction for fluid flow therein, $\bar{U}$ = the mean velocity of the substantially pure water through the portion of each of the fluid passages having continuous boundary surface and a substantially constant cross-section in the mean direction for fluid flow therein, $\rho$ = the density of the substantially pure water, $\mu$ = the absolute viscosity of the substantially pure water, $\Delta E_2$ = a static pressure differential between the substantially pure water at or upstream of the fluid inlet to the casing and the substantially pure water within each fluid passage at a position within the portion having continuous boundary surface and a substantially constant cross-section in the mean direction for fluid flow therein and where the flow rate is $G_2$ as previously defined immediately above and which is downstream of an outlet end of the flared entry portion by at least an amount $L_e$ and is determined in consistent units by the relationship:

$L_e = 0.04 R_e h$ when the Reynolds number, $R_e$, is that where the flow rate is $G_2$ as previously defined immediately above in the portion of each fluid passage having continuous boundary surface and a substantially constant cross-section in the mean direction for fluid flow therein, $K_2$ is a constant and is defined in consistent units, $$K_2 = \frac{\Delta E_1 - \Delta E_2 \left(\frac{G_1}{G_2}\right)^2}{G_1 - \frac{(G_1)^2}{G_2}}, \text{ where}$$

$G_1$ = the mass flow rate of the substantially pure water through each of the fluid passages when the Reynolds number $R_e$, is less than $C_2$ and is at least 1000 in the portion of each fluid passage having continuous boundary surface and a substantially constant cross-section in the mean direction for fluid flow therein, and $\Delta E_1$ = a static pressure differential between the substantially pure water at or upstream of the fluid inlet to the casing and the substantially pure water within each fluid passage at a position within the portion having continuous boundary surface and a substantially constant cross-section in the mean direction for fluid flow therein and where the flow rate is $G_1$ as previously defined immediately above and which is downstream of the outlet end of the flared entry portion by at least an amount $L_e$ as previously defined, and where the flared entry portion "figure of merit", M, is within the limits determined by the relationship in consistent units:

$$M < 1.36 \frac{h}{d_h}, \text{ where}$$

$d_h$ = the hydraulic diameter of the portion of each fluid passage having continuous boundary surface and a substantially constant cross-section in the mean direction for the flow of fluid therein, and is defined in consistent units by, $$d_h = \frac{4A}{C}, \text{ where}$$

A = cross-sectional area of the portion of each fluid passage having continuous boundary surface, and a substantially constant cross-section, normal to the mean direction for fluid flow therein, C = wetted perimeter of the portion of each fluid passage having continuous boundary surface and a substantially constant cross-section, in a plane normal to the mean direction for fluid flow therein, and where $h$ is as previously defined, and d. fluid pressure detecting means in the casing for detecting a fluid pressure differential in at least one of the fluid passages between spaced positions in the mean direction for fluid flow therein, at least one of the positions, being in a portion of that fluid passage having continuous boundary surface and a substantially constant cross-section, whereby e. the fluid characteristic to be measured is related to the pressure differential indicated by the pressure detecting means and is deducible therefrom in a consistent manner for any given fluid when laminar flow is maintained in the whole of each fluid passage.

Once a particular fluid passage geometry has been numerically evaluated by a static pressure differential measurement to meet the limiting criteria given above it will be appreciated that it is not necessary to numerically evaluate any other apparatus in this manner which has substantially the same fluid passage geometry. Thus any apparatus having substantially the same fluid passage geometry as a geometry so tested, may have fluid pressure detecting means provided solely for the purpose of providing a pressure differential from which the fluid characteristic to be measured may be deduced. It will be appreciated that once a particular fluid passage geometry has been tested, either static or total pressure detecting means may be provided for the purpose of providing a pressure differential from which the fluid characteristic to be measured may be deduced without invalidating the intent of the present invention.

Further, a fluid passage flared end geometry may be evaluated by different pressure measurements than those used to obtain a pressure differential to determine a fluid flow rate and/or viscosity. For example, for a prototype it may be convenient to evaluate the geometry from either a known entry or exit velocity to the fluid passage in which case only one pressure probe is necessary and this is disposed in the portion of the fluid passage having continuous boundary surface and a substantially constant cross-section, however, when apparatus using that flared entry geometry is to measure fluid flow rate and/or viscosity it may be advantageous for two pressure probes to be used in the fluid passage with at least one located in the portion of the fluid passage having continuous boundary surface and a substantially constant cross-section.

The apparatus according to the present invention ensures that:

1. a pressure differential is generated between two detector locations by means of wall boundary layer induced viscous shear energy dissipation in the fluid passage.

2. the pressure differential between the two suitably located pressure detectors is a large portion of the pressure differential as measured between the inlet to the fluid passage and the outlet from the fluid passage by minimizing viscous entry losses.

3. repeatable performance results are obtained in relation to well known manufacturing techniques such as metal pressing, die casting, plastic molding, powder metal forming, etc.

In some embodiments of the present invention the portion of the or each fluid passage having continuous boundary surface and a substantially constant cross-section has a magnitude of mean breadth which is at least as large as that given by a mean breadth to mean width ratio of 2:1.

In other embodiments of the present invention the portion of the or each fluid passage having continuous boundary surface and a substantially constant cross-section has a magnitude of mean breadth which is at least as large as that given by a mean breadth to mean width ratio of 3.0:1. In which case $G_1$ = the mass flow rate of the substantially pure water through the or each fluid passage when the Reynolds number, $R_3$, is preferably 1500 in the portion of the or each fluid passage having continuous boundary surface and a substantially constant cross-section in the mean direction for fluid flow therein, and $G_2$ = the mass flow rate of the substantially pure water through the or each fluid passage when the Reynolds number, $R_e$, is preferably 3000 in that portion of the or each fluid passage having continuous boundary surface and a substantially constant cross-section in the mean direction for fluid flow therein.

In other embodiments of the present invention the portion of the or each fluid passage having continuous boundary surface and a substantially constant cross-section has a magnitude of mean breadth which is at least as large as that given by a mean breadth to mean width ratio of 5:1. In which case $G_1$ = the mass flow rate of the substantially pure water through the or each fluid passage when the Reynolds number, $R_e$, is preferably 2000 in the portion of the or each fluid passage having continuous boundary surface and a substantially constant cross-section in the mean direction for fluid flow therein, and $G_2$ = the mass flow rate of the substantially pure water through the or each fluid passage when the Reynolds number, $R_e$, is preferably 4000 in that portion of the or each fluid passage having continuous boundary surface and a substantially constant cross-section in the mean direction for fluid flow therein.

In other embodiments of the present invention the portion of the or each fluid passage having continuous boundary surface and a substantially constant cross-section has a magnitude of mean breadth which is at least as large as that given by a mean breadth to mean width ratio of 10:1. In which case $G_1$ = the mass flow rate of the substantially pure water through the or each fluid passage when the Reynolds number, $R_e$, is preferably 3000 in the portion of the or each fluid passage having continuous boundary surface and a substantially constant cross-section in the mean direction for fluid flow therein, and $G_2$ = the mass flow rate of the substantially pure water through the or each fluid passage when the Reynolds number, $R_e$, is preferably 6,000 in that portion of the or each fluid passage having continuous boundary surface and a substantially constant cross-section in the mean direction for fluid flow therein.

Figure 2:
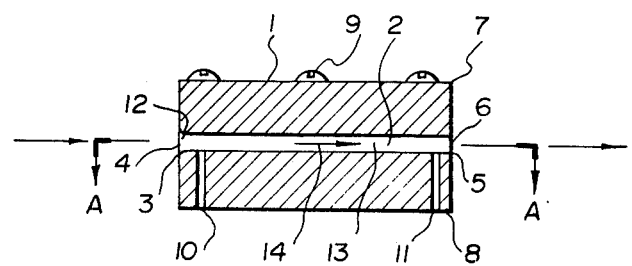
Figure 3:
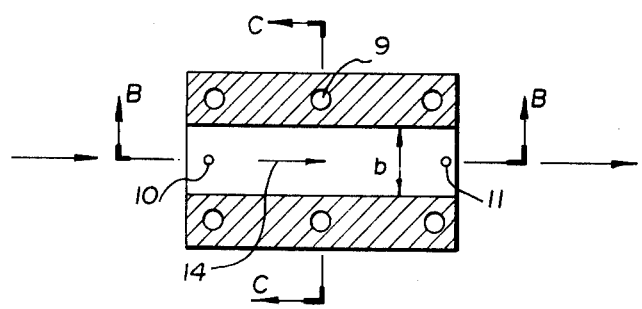
Figure 4:
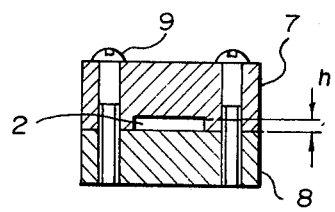
Figure 8:
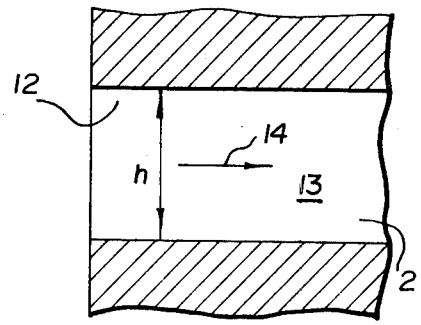
Figure 9:
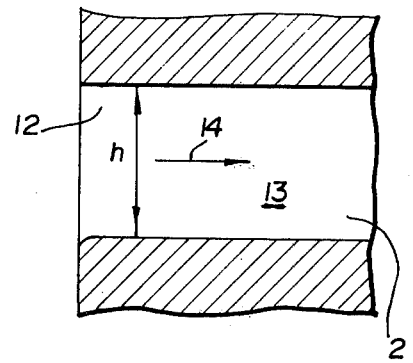
Figure 10:
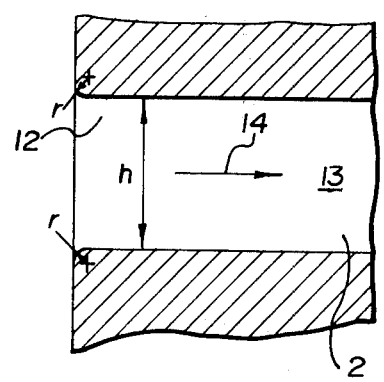
Figure 17:
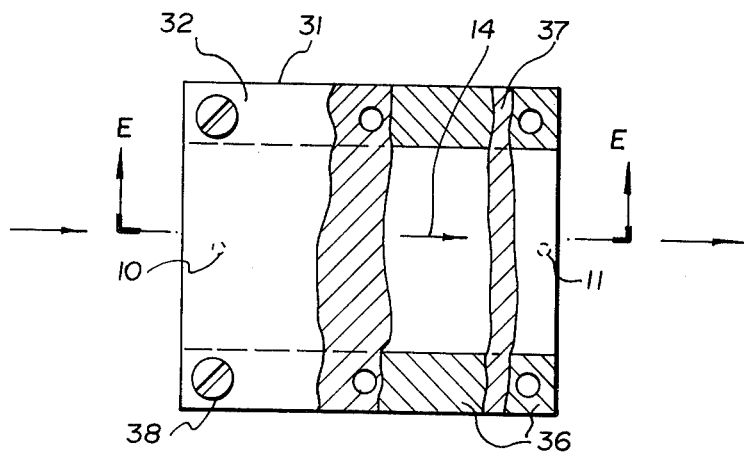
Figure 18:
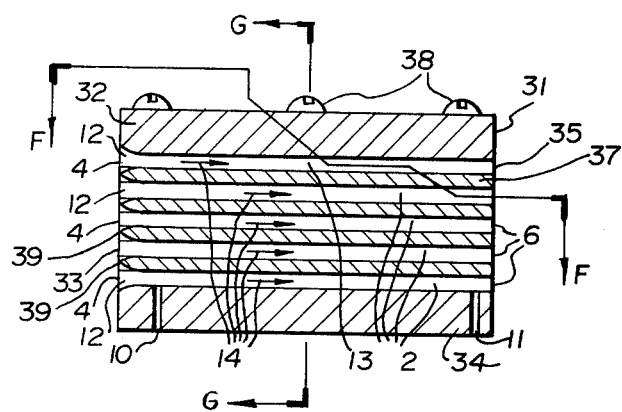
Figure 19:
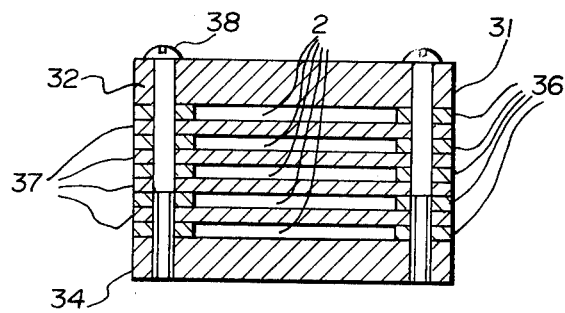
Figure 20:
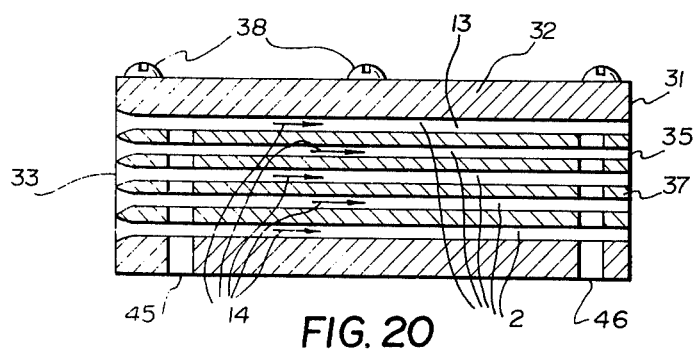
Figure 21:
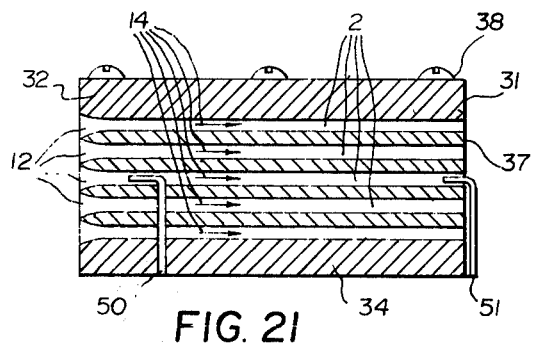
Figure 23:
Figure 24:
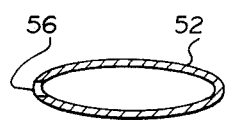
Figure 22:
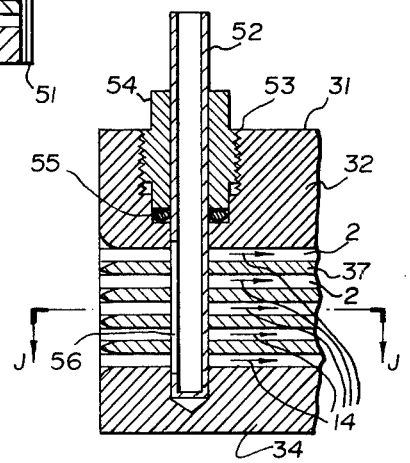
Figure 25:
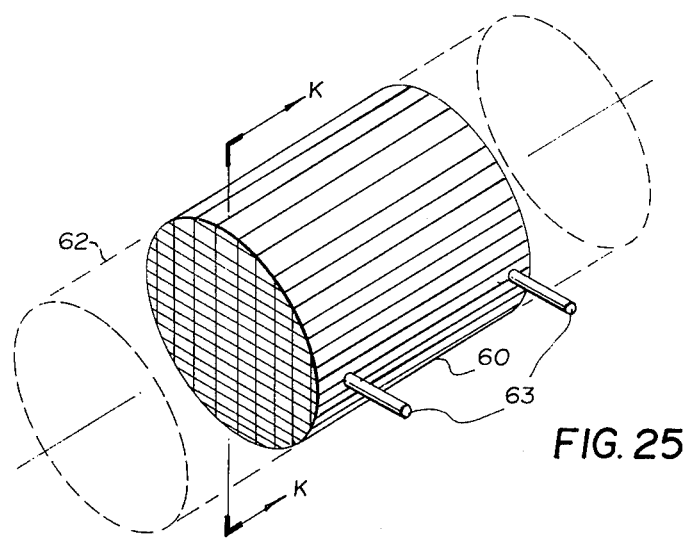
Figure 26:
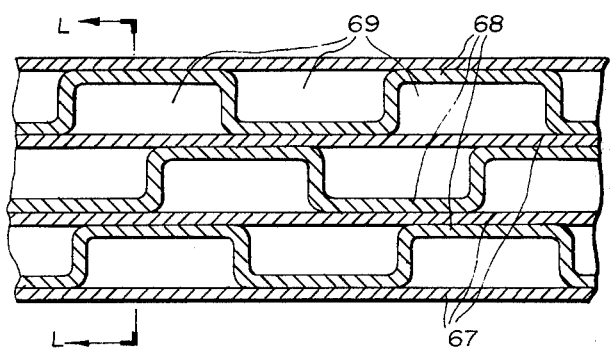
Figure 27:
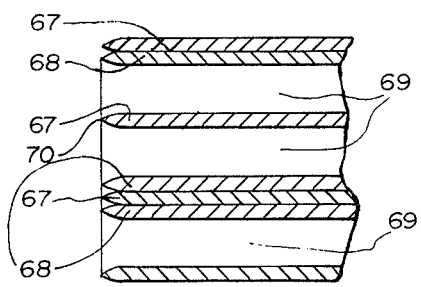
Figure 28:
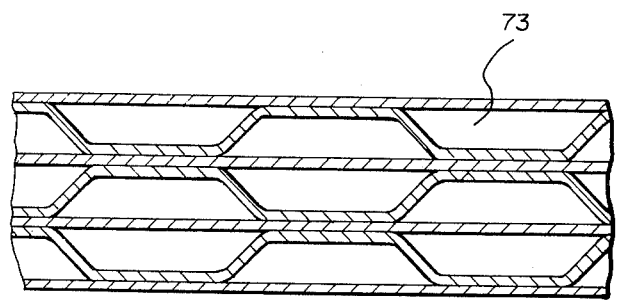
Figure 29:
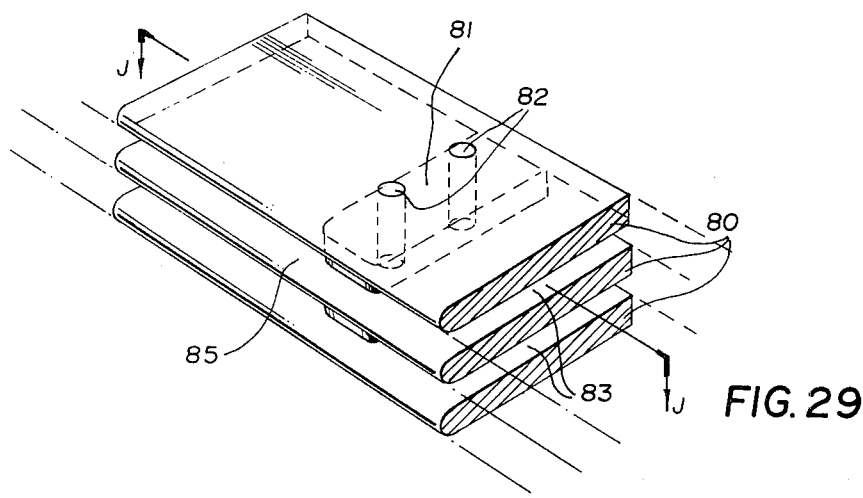
Figure 30:
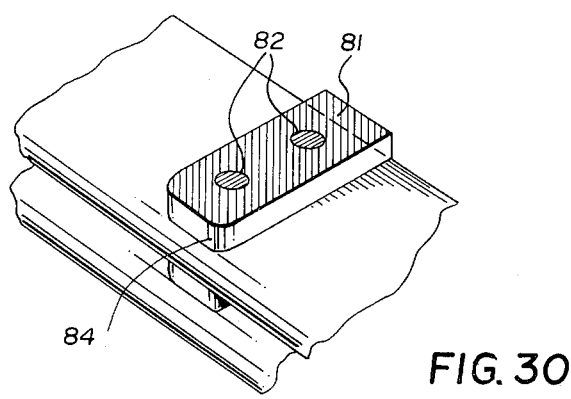
Figure 31:
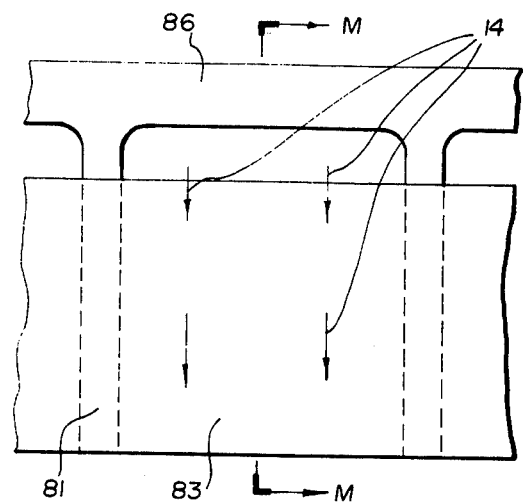
Figure 32:
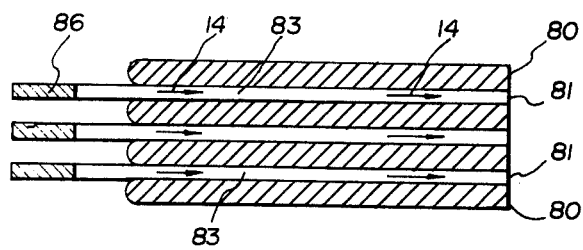
Figures 33, 34:
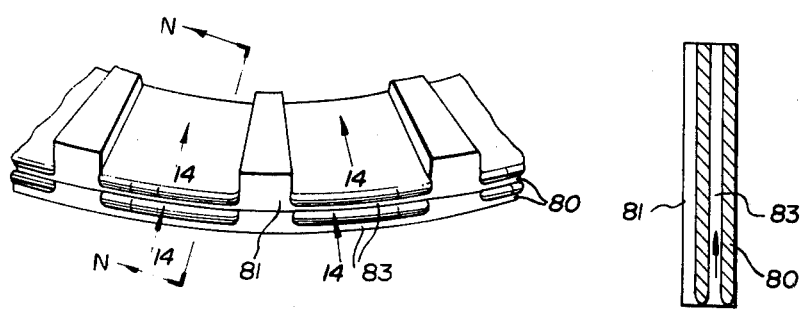
Figure 35:
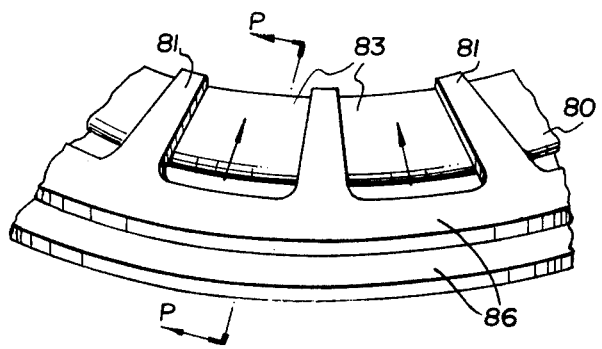
Figure 36:
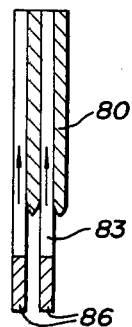
Figure 37:
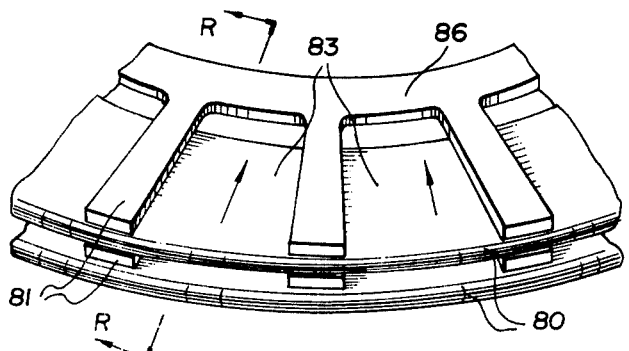
Figure 38:
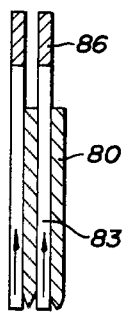
Figure 39:
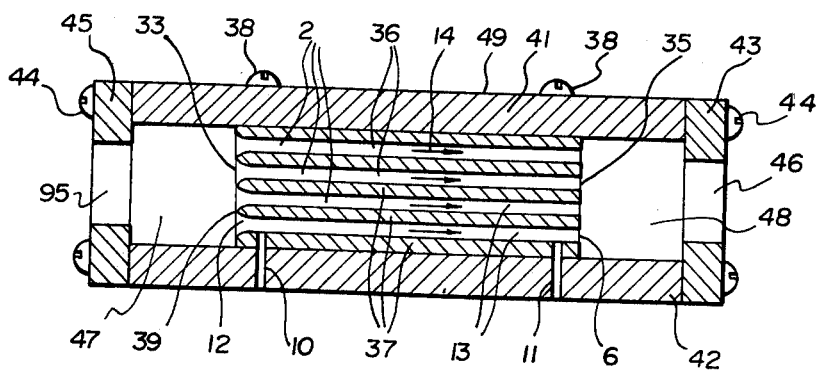
Figure 40:
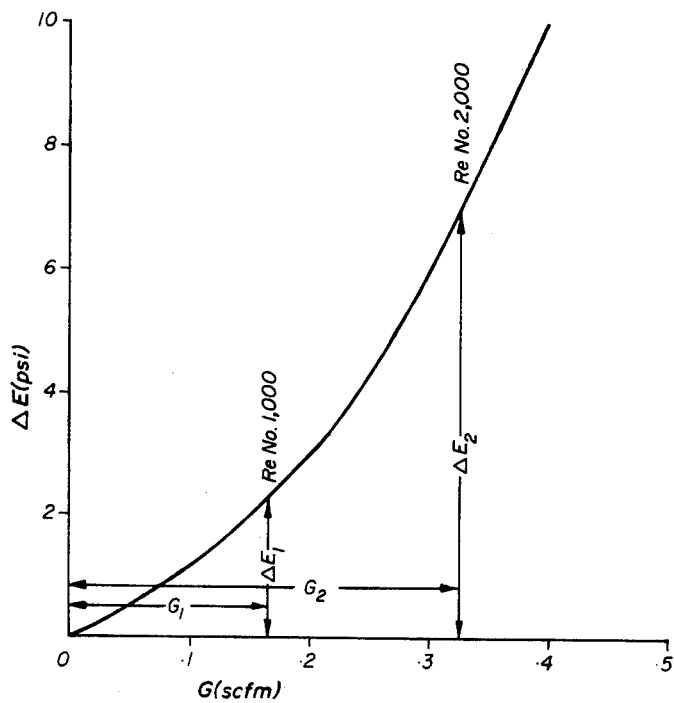
Figure 41:
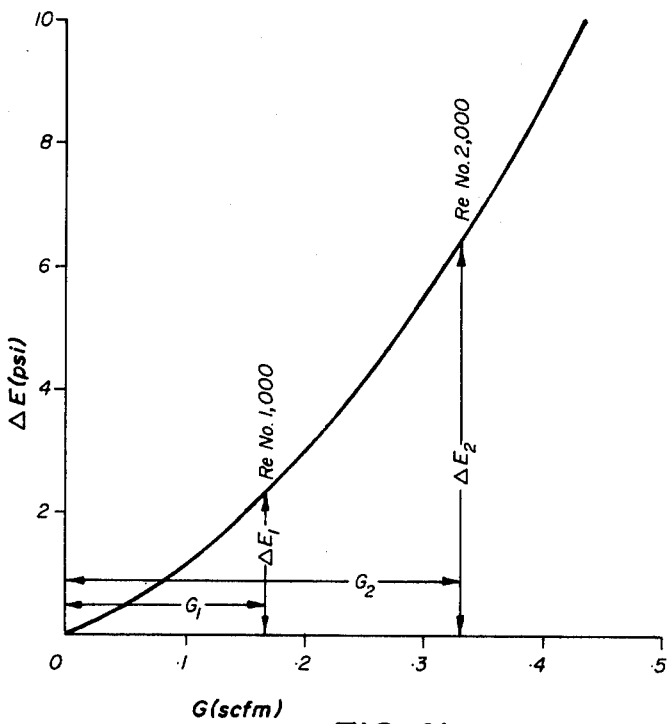
Figure 42:
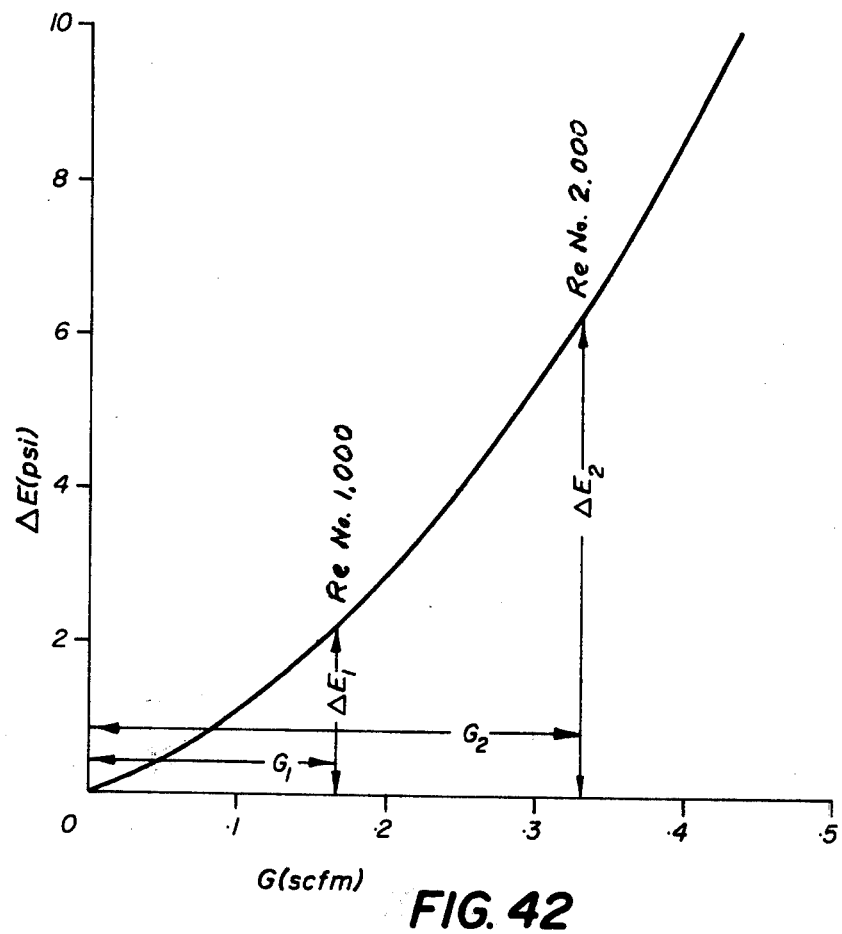

In the accompanying drawings which illustrate, by way of example, embodiments of the present invention as well as unsuitable flared entry portions, FIG. 1 is a diagrammatic view of an apparatus for measuring the flow rate and/or viscosity of a fluid, FIG. 2 is a sectional side view along B—B, FIG. 3, of an apparatus for measuring the flow rate and/or viscosity of a fluid and having a fluid passage comprising a flared entry portion leading to a single, laminar fluid flow portion, FIG. 3 is a sectional plan view along A—A, FIG. 2, FIG. 4 is a sectional end view along C—C, FIG. 3, FIGS. 5 to 16 are sectional side view of different entry portions to that shown in FIG. 2, some of which are suitable and others of which are unsuitable for use in the present invention, FIG. 17 is a partly sectional plan view of an apparatus similar to that shown in FIGS. 2 to 4, but having five fluid passages, along F—F, FIG. 18, FIG. 18 is a sectional side view along E—E, FIG. 17, FIG. 19 is a sectional end view along G—G, FIG. 18, FIG. 20 is a sectional side view of an apparatus similar to that shown in FIG. 18, but with enlarged static pressure taps extending to all of the fluid passages, FIG. 21 is a sectional side view of an apparatus similar to that shown in FIG. 18, but with total pressure probes, FIG. 22 is a sectional side view of a portion of the apparatus shown in FIG. 18 but showing a total pressure probe, FIG. 23 is a sectional view along J—J, FIG. 22, of the total pressure probe, FIG. 24 is a sectional view along J—J, FIG. 22, of a different shape of total pressure probe, FIG. 25 is a diagrammatic view of an apparatus for measuring the flow rate and/or viscosity of a fluid having a matrix of fluid passages, FIG. 26 is a sectional end view along K—K, FIG. 25, FIG. 27 is a sectional side view along L—L, FIG. 26, of a flared entry portion, FIG. 28 is a sectional end view along K—K, FIG. 25, but showing trapezoidal fluid passages, FIG. 29 is a pictorial view of a portion of the apparatus shown in FIG. 18, showing a different construction for rectangular fluid passages, FIG. 30 is a pictorial view of a portion of the apparatus along J—J, FIG. 29, with a top plate removed, FIG. 31 is a plan view of a portion of an apparatus similar to FIGS. 29 and 30, but with integral shim members, FIG. 32 is a side sectional view along M—M, FIG. 31, FIG. 33 is an isometric view of a portion of an apparatus which is similar to that shown in FIG. 29, but with shims and spacers integral and with the mean directions for fluid flow in the fluid passages radiating from a central position, FIG. 34 is a sectional end view along N—N, FIG. 33, FIG. 35 is an isometric view of an apparatus which is similar to that shown in FIGS. 31 and 32, but with a shim ring member upstream of the passage inlet and joining all of the shims, FIG. 36 is a sectional end view along P—P, FIG. 35, FIG. 37 is a pictorial view of apparatus similar to that shown in FIGS. 31 and 32, but with a shim ring member downstream of the passage outlet and joining all of the shims, FIG. 38 is a sectional end view along R—R, FIG. 37, FIG. 39 is a sectional side view of an apparatus similar to that shown in FIGS. 17 to 19 but having inlet and outlet cavities in the casing, FIG. 40 is a graph of the pressure drop/flow rate characteristic of a fluid passage of rectangular cross-section and having a square entry portion as shown in FIG. 8, FIG. 41 is a similar graph to that shown in FIG. 40 for a similar fluid passage but having a radiused entry portion as shown in FIG. 10, and FIG. 42 is a similar graph to that shown in FIG. 40 for a similar fluid passage but having a chamfered inlet as shown in FIG. 11.

Referring now to FIG. 1 there is shown an apparatus for measuring the flow rate and/or viscosity of a fluid comprising:

a. a casing 1 having a fluid passage 2, which is elongated in cross-section normal to the mean direction, arrow 14, for fluid flow therein with two parallel, opposed major boundary surface portions 21 and 22, which are parallel in a plane normal to the mean direction for fluid flow therebetween, the fluid passage comprising a flared entry portion 12 of length $L_f$ and a portion 13 of length $L_c$ having, in the mean direction for fluid flow therein, continuous boundary surface and a substantially constant cross-section, the flared entry portion 12 being flared to decrease in width, without increasing in breadth, in the mean direction for fluid flow therein and forming an unobstructed flow path to the portion 13 having, in the mean direction for fluid flow therein, a continuous boundary surface and a substantially constant cross-section, a fluid inlet 3 to the casing and forming a substantially unobstructed flow path for fluid to the whole area at an inlet end 4 to the flared entry portion 12 of the fluid passage 2, said inlet area being normal to the mean direction for flow of fluid through that end 4 of the flared entry portion 12, and a fluid outlet 5 from the casing and forming a substantially unobstructed flow path for fluid from the whole area at an outlet end 6 of the fluid passage 2 said outlet area being normal to the mean direction for flow of fluid at the outlet end 6 of the fluid passage 2, and wherein, b. the portion 13 of the fluid passage 2 having continuous boundary surface and a substantially constant cross-section in the mean direction for fluid flow therein has a magnitude of mean breadth $b$ which is at least as large as that given by a mean breadth $b$ to mean width $h$ ratio of 1.5 to 1, (shown having a mean breadth to mean width ratio of about 3:1) and an area in any plane normal to the mean direction for fluid flow therein which does not vary more than in the region of 2% from the mean area calculated in this manner for the whole length $L_c$ of the said portion having continuous boundary surface and a substantially constant cross-section, and wherein c. the geometry of the flared entry portion 12 of the fluid passage 2 is such that, when laminar flow is maintained in the whole of the fluid passage 2, using substantially pure water at 70° F. as a standard, the flared entry portion 12 has a "figure of merit", M which is calculated using consistent units from the relationship:

$$M = 1 - \frac{K_2 G_2}{\Delta E_2}$$

where, $G_2$ = the mass flow rate of the substantially pure water through the fluid passage 2 when the Reynolds number, $R_e$, is at least 2000 in the portion 13 of the fluid passage 2 having continuous boundary surface and a substantially constant cross-section in the mean direction for fluid flow therein, and the Reynolds number, $R_e$, in the portion 13 of the fluid passage having continuous boundary surface and a substantially constant cross-section is defined in consistent units by the relationship:

$$R_e = \frac{h \bar{U} \rho}{\mu}, \text{ where}$$

$h$ = the width separating the parallel opposed major boundary surface portions, of the portion of the fluid passage having continuous boundary surface and a substantially constant cross-section in the mean direction for fluid flow therein, $\bar{U}$ = the mean velocity of the substantially pure water through the portion 13 of the fluid passage having continuous boundary surface and a substantially constant cross-section in the mean direction for fluid flow therein, $\rho$ = the density of the substantially pure water, $\mu$ = the absolute viscosity of the substantially pure water, $\Delta E_2$ = a static pressure differential between the substantially pure water at or upstream of the fluid inlet 3 to the casing 1 and the substantially pure water within the fluid passage 2 at a position within the portion 13 having continuous boundary surface and a substantially constant cross-section in the mean direction for fluid flow therein and where the fluid flow rate is $G_2$ as previously defined immediately above and which is downstream of an outlet end 23 of the flared entry portion by at least an amount $L_e$ and is determined in consistent units by the relationship:

$L_e = 0.04\, R_e h$ when the Reynolds number, $R_e$, is that where the flow rate is $G_2$ as previously defined immediately above in the portion 13 of the fluid passage having continuous boundary surface and a substantially constant cross-section in the mean direction for fluid flow therein, $K_2$ is a constant and is defined in consistent units by:

$$K_2 = \frac{\Delta E_1 - \Delta E_2 \left(\frac{G_1}{G_2}\right)^2}{G_1 - \frac{(G_1)^2}{G_2}}, \text{ where}$$

$G_1$ = the mass flow rate of the substantially pure water through the fluid passage 2 when the Reynolds number $R_e$, is at least 1000 in the portion 13 of the fluid passage having continuous boundary surface and a substantially constant cross-section in the mean direction for fluid flow therein, and $\Delta E_1$ = a static pressure differential between the substantially pure water at or upstream of the fluid inlet 3 to the casing 1 and the substantially pure water within the fluid passage at a position within the portion 13 having continuous boundary surface and a substantially constant cross-section in the mean direction for fluid flow therein and where the flow rate is $G_1$ as previously defined immediately above and which is downstream of the outlet end of the flared entry portion 12 by at least an amount $L_e$ as previously defined, and where the flared entry portion "figure of merit", M, is within the limits determined by the relationship in consistent units:

$$M < 1.36 \frac{h}{d_h}, \text{ where}$$

$d_h$ = the hydraulic diameter of the portion 13 of the fluid passage 2 having continuous boundary surface and a substantially constant cross-section in the mean direction for the flow of fluid therein, and is defined in consistent units by:

$$d_h = \frac{4A}{C}, \text{ where}$$

A = cross-sectional area of the portion 13 of the fluid passage 2 having continuous boundary surface, and a substantially constant cross-section, normal to the mean direction for fluid flow therein, C = wetted perimeter of the portion 13 of the fluid passage 2 having continuous boundary surface and a substantially constant cross-section, in a plane normal to the mean direction for fluid flow therein, and where $h$ is as previously defined, and d. fluid pressure detecting means, in this embodiment in the form of static pressure probes 10 and 11 in the casing 1, connected to a differential pressure gauge 24, for detecting a fluid pressure differential in the fluid passage 2, between spaced positions in the mean direction, arrow 14, for fluid flow therein, at least one of the positions being in the portion 13 having continuous boundary surface and a substantially constant cross-section, whereby e. the fluid characteristic to be measured is related to the pressure differential indicated by the fluid pressure means, that is static pressure probes 10 and 11, and is deducible therefrom in a consistent manner for any given fluid when laminar flow is maintained in the whole of fluid passage 2.

When the fluid pressure detecting means comprises static pressure probes 10 and 11, the static pressure is measured preferably at the boundary surface of the fluid passage 2 and preferably at the centre of the fluid passage breadth.

However, when the fluid pressure detecting means detects fluid total pressure, as will become apparent with further description of other embodiments of the present invention, the total pressure is preferably measured in the vicinity of the center of the fluid passage breadth with detecting means oriented so as to have maximum sensitivity in the local mean direction of flow as shown by arrows 14 in FIG. 1. When the entrance to the total head detecting means is less than the passage width such entrance should be preferably located in the vicinity of the centre of the passage width and breadth and should be oriented to have maximum sensitivity.

The fluid pressure tap 10 is located within the fluid passage 2 and upstream of fluid pressure tap 11 and preferably at a minimum distance from the inlet end 3 of the fluid passage 2 such that when using substantially pure water at 70° F. as a standard, then a figure of merit, T, for a suitable upstream position, but not necessarily the only position, for the pressure probe 10 may be evaluated from the following relationship in consistent units:

$$T = \frac{F_1 G_2}{F_2}$$

where, in consistent units, $$F_2 = \frac{\Delta C_1 - \Delta C_2 \left(\frac{G_1}{G_2}\right)^2}{G_1 - \frac{(G_1)^2}{G_2}}$$

where $G_1$ and $G_2$ are as previously defined for the appropriate mean breadth, $b$, to the mean width, $h$, ratio $\Delta C_1$ = pressure differential between the upstream pressure probe, such as 10 shown in FIG. 1, and the downstream pressure probe, such as 11 as shown in FIG. 1, when the flow rate in the portion 13 of the fluid passage 2 having substantially constant cross-section is $G_1$ defined immediately above, $\Delta C_2$ = pressure differential between the upstream pressure probe 10 and the downstream pressure probe 11 and when the flow rate in the portion 13 of the fluid passage having substantially constant cross-section is $G_2$ as defined immediately above, and where, in consistent units:

$$F_1 = \frac{\Delta C_2 - F_2(G_2)}{(G_2)^2}$$

where $\Delta C_2$, $F_2$ and $G_2$ are as previously defined immediately above.

In applications where linearity of output pressure differential on the measured characteristic is important the calculated upstream pressure tap figure of merit may suitably be limited by the relationship:

$T < 0.0015$

If T exceeds 0.0015, the upstream pressure probe 10 may be moved further downstream in order to reduce the calculated value of T to less than 0.0015. However, in applications where output differential pressure sensitivity to the measured fluid characteristic is important, it may be advantageous to locate the upstream pressure probe 10 such that the figure of merit will exceed 0.0015.

This apparatus in accordance with FIG. 1, uses the flared inlet portion 12 to the substantially constant cross-section laminar flow portion 13 to reduce the pressure loss across the entire fluid passage, from the area of inlet end 3 to the area of the outlet end 5 such that this pressure loss tends to approach the usable output differential pressure magnitude. This differentiates the laminar flow measurement apparatus of the present invention from other known laminar flow measurement devices which do not define a flared inlet portion 12 to the or each fluid passage 2 for the laminar flow of fluid therein.

The operational principle of the present invention can be most easily understood by considering the constant area portion 13 of fluid passage 2. In the absence of a flared inlet portion 12, it is known that a pressure loss is induced over an inlet portion of the fluid passage 2 which is in excess of the pressure loss induced over any equivalent length of substantially identical fluid passage downstream of the inlet portion. If will be appreciated that this excess of pressure loss, which is commonly referred to as "the entrance pressure loss", is additional to the static pressure loss ($\Delta p$) resulting from the conversion of static pressure upstream of the fluid passage inlet to fluid velocity within the fluid passage in accordance with the well-known Bernoulli relationship in consistent units:

$$\Delta p = \frac{1}{2} \rho \frac{V^2}{g}$$

where $\rho$ = density of the fluid flowing through the passage,

V = mean velocity of the fluid flowing through the constant area portion of the passage, $g$ = acceleration due to gravity In the apparatus according to the present invention, the inlet portion 12 is flared such that the laminar flow velocity profiles in planes normal to the mean direction for fluid flow tend to reduce the fluid acceleration gradients within the inlet portion 12 and consequently reduce the associated fluid viscous shear induced pressure losses which are in addition to those fluid viscous shear induced pressure losses which would be generated over an equivalent length of substantially constant cross-section fluid passage having identical geometry, but being downstream of the inlet portion 12.

It is therefore possible with the present invention to measure the flow rates of fluids wherein the usable output differential pressure, which is the measure of the laminar fluid flow rate through the apparatus, tends to more closely approach in magnitude, the pressure loss induced by the complete apparatus than for other known laminar flow rate measurement apparatus. Accordingly, an advantage of the present invention is the limited pressure loss imposed on the laminar fluid flow whose rate is being measured while an adequate output signal sensitivity to flow rate is ensured.

This advantage is particularly useful in applications where the power loss, as indicated by the product of the pressure loss across the complete apparatus and the flow rate through the apparatus, must be maintained small due to particular application power availability constraints and where sizeable flow rate dependent output signal differential pressure is required for purposes of reducing the sensitivity requirement of associated indicating and signal transmitting apparatus.

Typical applications where the use of the present invention has particular advantages are:
1. gas pipeline flow rate measurement
2. cooling fluid flow rate measurement in combustion and power generation applications
3. intake air flow rate measurement to internal combustion engines
4. process industry fluid transfer pipeline flow rate measurement Additionally, it has been found in practice that minor boundary surface imperfections such as scratches, burrs, dents, etc. in the immediate inlet region of a laminar flow passage result in disproportionately large pressure drops additional to the pressure drop occuring when using a boundary surface without such imperfections. In the present invention, the flared inlet portion has been found to have the effect of very substantially reducing the pressure drop associated with such inlet boundary wall imperfections as may occur as a result of practical apparatus fabrication and application.

The present invention, when used as a viscometer, provides a differential pressure output signal that is proportional to fluid viscosity for a given constant volumetric flow rate of fluids on either a continuous or intermittent basis. Further, the larger wetted surface area of the laminar flow passage compared to the wetted surface area of laminar flow passages having substantially circular cross-sections such as capillary tube viscometers, facilitates fluid temperature regulation.

Further, it will be appreciated that the performance of apparatus according to the present invention is not in general dependent upon the orientation of the apparatus with respect to gravity or other accelerations in that compensation for orientation will not be required unless hydrostatic head effects vary significantly either along or across the flow length of the fluid passage 2. For example, such hydrostatic head variations might be encountered in the particular case of a large scale apparatus, according to the present invention, operating with a high density fluid and oriented with the direction for fluid flow in the passage 2 being vertical. An apparatus according to the present invention and having a plurality of similar fluid passages, such as will be described later with reference to other figures, may also be affected by hydrostatic head variations in the same manner.

It will be further appreciated, and will become more apparent with following description of particular embodiments of the present invention, that the apparatus may be very economically fabricated using a suitable assembly comprising plates, strips, discs and/or rings which have been edge profiled by such well-known manufacturing techniques as rolling, extruding, coining, turning, milling, tumbling, etc.

In FIGS. 2 to 4 similar parts to those shown in FIG. 1 are designated by the same reference numerals and the previous description is relied upon to describe them.

In FIGS. 2 to 4 the casing 1 comprises a top plate 7 affixed to a bottom plate 8 by screws 9 which are screwed into threaded holes in the bottom plate 8. The top plate 7 is suitably sealed to the bottom plate 8 to provide adequate sealing of the fluid passing through the fluid passage 2.

The apparatus according to the present invention, has been found in practice to have a useful output differential pressure dependency upon flow rate through the apparatus while exhibiting decreased pressure loss across the entire fluid passage 2 relative to other known laminar flow rate and/or viscosity measurement apparatus, such as the apparatus described in the above noted patents, provided that:

1. portion 13, of the fluid passage 2, downstream and connected without discontinuity to the entry portion 12, has a substantially constant cross-section as previously defined,
2. the entry portion 12, of the fluid passage 2, leading to the substantially constant cross-section portion 13 of the fluid passage, is flared such that when using substantially pure water at 70° F., for example distilled water, as a standard, the flared entry figure of merit, M, previously defined, shall meet the limiting criteria previously defined as per c) above.

It has been found convenient in practice to numerically evaluate the geometry of the flared inlet portion 12 of the fluid passage 2 in terms of the limiting criteria as per provision c) above when the output differential pressure is measured by two static pressure taps, one of which is in communication with the inlet 4 to the flared entry portion 12 of fluid passage 2 and is arranged to measure the static pressure at or upstream of the inlet 4 and the other is located within the substantially constant cross-section fluid passage 13 at the previously defined distance $L_e$ downstream of the outlet end of the flared portion of the said passage by means of the following procedure.

The mass flow rate of substantially pure water, such as distilled water, at 70° F. corresponding to Reynolds numbers of 1,000 and 2,000 within the substantially constant cross-section portion 13 of fluid passage 2 is determined using any well known measurement means, such as a rotameter, or by volumetric accumulation of the water flowing from the fluid passage 2 over a known time, for the particular geometry of fluid passage 2 where the viscosity and density of substantially pure water, for example distilled water at 70° F. may be taken, in English units to be $0.210 \times 10^{-4}$ lbs. sec/ft$^2$ and 62.4 lbs./ft$^3$ respectively.

The output differential static pressure for water mass flow rates corresponding to two Reynolds numbers, in the substantially constant cross-section portion 13 of the fluid passage 2, for the appropriate breadth $b$ to mean width $h$ ratio, are determined using well known precision pressure measurement means such as manometers, pressure transducers or similar means as will be known to those skilled in the art.

The entry portion figure of merit, M, is numerically evaluated from the output differential static pressure measurement and corresponding mass flow rate corresponding to the two Reynolds numbers for the appropriate mean breadth $b$ to mean width $h$ ratio in accordance with the previously defined relationship.

Should the magnitude of the previously defined figure of merit, M, violate the limiting criteria, then the said criteria could be satisfied by enlarging the profile defining the flared entry portion 12 either with or without altering the shape of the contour of the flared entrance portion 12.

The fluid static pressure tap 11 is located within the substantially constant cross-section portion 13 of passage 2 and downstream of fluid pressure tap 10 and preferably as close as possible to the outlet end 6 of the constant cross-section portion 13 of fluid passage 2 within the constraint of practical fabrication limitations. The position of the fluid static pressure tap 10 is chosen to be within the laminar flow fluid passage 2 as previously described with reference to FIG. 1.

In FIGS. 5 to 16 there are shown cross-sectional side views of a number of laminar fluid flow passages, each having a different configuration of entry portion and wherein similar parts to those shown in FIG. 1, are designated by the same reference numbers and the previous description is relied upon to describe them.

Figure 5:
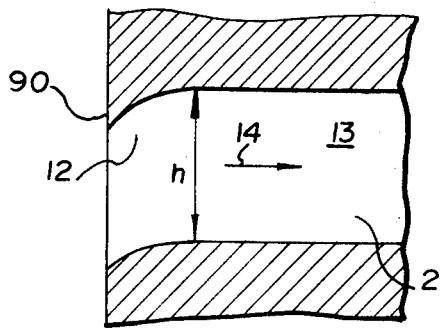

In FIG. 5, there is shown a fluid passage 2 having an inlet portion which has an inwardly extending lip 90 such as might be produced by a metal shearing process and which would not meet the criteria or figure of merit, (M), due in part to excessive flow velocity gradients in the immediate vicinity of the lip and due in part to the non-symmetry of the entrance flow.

Figure 6:
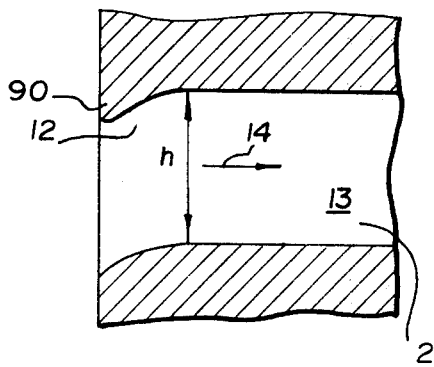
Figure 7:
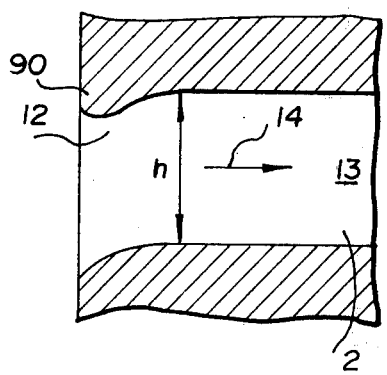

In FIGS. 6 and 7 the lip 90 has been rounded but would still not meet the criteria for the figure of merit, M, for the same reason as given for FIG. 5.

In FIG. 8 there is shown a fluid passage 2 having a squared inlet portion, and which would not meet the criteria for the figure of merit, M, even though the flow velocity gradients in the vicinity of the squared corners are reduced relative to those gradients associated with the inlet portion shown in FIG. 5 and the entrance flow is symmetrical.

In FIG. 9 there is shown a fluid passage 2 having an inlet portion with the lower portion of the lip rounded and the upper portion of the lip squared and which would not meet the criteria for the figure of merit, M, due in part to nonsymmetry of entrance flow and in part due to the high flow velocity gradient in the vicinity of the squared corner.

In FIG. 10 there is shown a fluid passage 2 in accordance with the present invention having a radiused flared entry portion. Any radii $r$ will give an improvement over the squared inlet portion shown in FIG. 8.

In FIG. 11 there is shown a fluid passage 2 in accordance with the present invention having a chamfered inlet portion. Any depth $d$ will give an improvement over the squared inlet portion shown in FIG. 8.

In FIG. 12 there is shown a fluid passage 2 according to the present invention having a chamfered inlet portion with the upstream end of the chamfer rounded. Such rounding of the inlet end of the entry portion would further improve the figure of merit relative to an entry portion of the type shown in FIG. 11 having the same chamfer.

In FIG. 13 there is shown a fluid passage 2 in accordance with the present invention having a chamfered outlet portion with the downstream end of the chamfer rounded. Such rounding of the inlet end of the entry portion would further improve the figure of merit relative to an entry portion of the type shown in FIG. 11 having the same chamfer.

In FIG. 14 there is shown a fluid passage 2 according to the present invention having a chamfered inlet portion which is rounded on both the upstream and downstream ends. Such rounding of the inlet and outlet end of the entry portion would further improve the figure of merit relative to entry portions of both of the types shown in FIGS. 12 and 13 and having the same chamfer.

In FIG. 15 there is shown a fluid passage 2 according to the present invention having a double chamfered inlet portion with the upstream angle having a steeper angle than the downstream chamfer. Such double chamfering of the inlet portion would also improve the figure of merit relative to the entry portion in FIG. 11 provided that the angle of the second chamfer is not steeper than the angle of the single chamfer of FIG. 11.

In FIG. 16 there is shown a flared entry portion in accordance with the present invention, where the radius of curvature of the flare changes in magnitude over at least a portion of the inlet length. The flow velocity gradients throughout the flared entry portion may be minimized by appropriately contouring the inlet portion in this manner, the contour of which may be determined by tests.

In practice it has been found that a gradual and continuous increase in the radius of curvature of the flare in the direction for fluid flow gives good results in terms of the figure of merit, M.

In FIGS. 17 and 19 similar parts to those shown in FIG. 1 are designated by the same reference numerals and the previous description is relied upon to describe them.

There is shown in FIGS. 17 to 19 three views of an apparatus for flow rate and/or viscosity measurement of fluid having a plurality of substantially identical flow passages. The apparatus comprises a casing generally designated 31, a plurality of fluid passages typically designated 2, a whole fluid inlet area 33 which may be exposed to a source of pressurized fluid, which may be an ambient fluid such as the atmosphere, and forming a substantially unobstructed flow path for fluid to the whole area of the individual inlet ends 4 to the said fluid passage where the said inlet area 33 is normal to the mean direction, as shown by arrows 14, of flow in the fluid passages 2, and a whole fluid outlet area 35 forming a substantially unobstructed flow path for fluid from the whole of the individual outlet ends 6 of the fluid passages 2 where the said outlet area 35 is normal to the mean direction for flow of fluid 14 in fluid passage 2, the whole outlet area 35 which is exposed to a sink for fluid that is at a pressure lower than that of the pressurized fluid at the fluid inlet area 33, such that there is a flow of fluid through passage 2 in the direction of arrows 14, and having a top cover plate 32, a bottom cover plate 34 and alternate shims 36, and separator plates 37, which together form inlet area 33 and outlet area 35 and the plurality of fluid passages 2 for laminar flow of fluid therethrough in the direction shown by arrows 14. The cover plates 32 and 34, shims 36 and separator plates 37 are located relative to each other, as shown in FIGS. 17, 18 and 19 and are clamped together in a fluid tight manner by means of screws 38 threaded into bottom plate 34.

In operation, pressurized fluid from a source (not shown) is supplied to the whole of the inlet area 33 of the casing 31 and flow through the individual inlet ends 4 of the fluid passages 2, through the inlet portion 12 of the fluid passages 2 and through the substantially constant cross-section portions 13 of the fluid passage 2 and through the individual passage outlet ends 6 to the whole outlet area 35 and to a fluid sink (not shown).

The separator plates 37 are profiled along their upstream edges 39 to form, the flared entry portion 12 to the substantially constant cross-section portion 13 of the fluid passages 2, as shown in FIG. 18. It will be appreciated that although the profile of the inlet portion 12 of the fluid passage 2 is, in general, similar to that shown in FIG. 1, the profile of the flared inlets could be any other suitable shape provided the flared entry portion 12 of the fluid passages 2 meets the figure of merit M, criteria previously defined.

There is shown in FIGS. 17, 18 and 19 an upstream static pressure tap 10 and a downstream static pressure tap 11 and wherein the downstream static pressure tap 11 is located as close as possible to the outlet end 6 of one of the constant cross-section portions of one of the fluid passages 2 within the constraint of practical fabrication limitations.

The upstream fluid static pressure tap 10 is located within the fluid passage 2 and upstream of fluid static pressure tap 11 and preferably at a minimum distance from the inlet end 4 of the fluid passage 2 such that when using substantially pure water, for example distilled water, at 70° F. as a standard then the upstream pressure tap figure of merit, T, previously defined, conforms with the previously given limit.

In the apparatus shown in FIGS. 17, 18 and 19 the differential pressure between static pressure taps 10 and 11 as measured by a differential pressure sensing means (not shown) is a proportional measure of the fluid flow rate or viscosity of the fluid passing through the apparatus from the whole inlet area 33 to the whole outlet area 35. Additionally, in this multipassage embodiment of the present invention the pressure loss across the entire apparatus from inlet area 33 to outlet area 35 is appreciably reduced relative to apparatus without such a flared inlet section by the use of the flared inlet section in accordance with the present invention.

In FIG. 20 similar parts to those shown in FIGS. 17, 18 and 19 are designated by the same reference numerals and the same description is relied upon to describe them.

FIG. 20 is a cross-sectional side view of an apparatus similar to that shown in FIGS. 17, 18 and 19 except that the static pressure taps 45 and 46 have a diameter several times the lesser dimension of the cross-section of the substantially constant cross-section portion 13 of fluid passage 2 normal to the direction for fluid flow therethrough and both pressure taps are shown extending through the separator plates 37 such that each passage 2 is in communication with the adjacent passage at each of the pressure taps. Such communication of the pressure taps with all of the fluid passages 2 minimizes the effects of manufacturing tolerance deviations between the flared inlet portions and substantially constant cross-section portions of the fluid passages 2. Further, each of the pressure taps may be in communication with from one to all of the fluid passages 2.

In FIG. 21 similar parts to those shown in FIGS. 17 to 19 are designated by the same reference numerals and the previous description is relied upon to describe them.

In FIG. 21 there is shown an apparatus similar to that shown in FIGS. 17 to 19 except that there is shown an upstream total pressure probe 50 and a downstream total pressure probe 51 whose inlets are located within at least one of the fluid passages 2 in accordance with the same criteria used to locate the static pressure probes 10 and 11 described with reference to and shown in FIGS. 17 to 19.

The embodiment shown in FIG. 21 operates in the same manner as the embodiment described with reference to FIGS. 17 to 19 and the output differential pressure is measured in the same manner and gives the same output proportionality to measured characteristic as the apparatus described with reference to FIGS. 17 to 19.

It will be appreciated that with any of the apparatus shown in FIGS. 17 to 19, 20 or 21, or with an apparatus similar to that shown in these figures but having a different number of parallel and identical fluid passages 2, the static pressure taps or total pressure probes could be located within any one or any number of the flow passages 2 in a particular apparatus because both the static pressure gradient and the total pressure gradient in the direction for fluid flow 14 within all the fluid passages will be essentially the same.

The embodiments of the present invention described with reference to any of FIGS. 17 to 21 when used as a viscometer provides a differential pressure output signal that is proportional to the absolute viscosity of the fluid passing therethrough for a given volumetric flow rate of fluids. Further the large surface area of the fluid passage 2 of the present invention, in contact with the fluid, facilitates temperature regulation of the fluid flowing therethrough.

In FIG. 22 similar parts to those shown in FIG. 21 are designated by the same reference numerals and the previous description is relied upon to describe them.

A specific total head pressure probe configuration is shown in FIGS. 22 and 23. A total head probe 52, is fixed within the apparatus by some suitable means such as a screw threaded plug 54, threaded into the aperture 53 in cover plate 32, and sealed therein by an 'O'-ring 55, and passing through separator plates 37 so as to traverse the fluid passages 2. A narrow longitudinal slot 56 is cut along a portion of the length of probe 52 and a section through the slotted tube is shown in FIG. 23. The probe 52 is located such that the slot 56 is oriented towards and is essentially perpendicular to the fluid flow direction within the fluid passages 2, as shown by the arrows 14. Two such probes are particularly useful in detecting the total pressure differential between any given locations within one or more identical flow passages with configurations of the apparatus as shown in FIG. 21, or in configurations similar to that shown in FIG. 21 but having different number of identical fluid passages than are shown in FIG. 21.

It will be appreciated that total head probe 52 need not be circular in cross-section as shown in FIG. 23, but may have other cross-sections such as the elliptical section as shown in FIG. 24, where similar parts as shown in FIG. 22 are designated by the same reference numerals and the previous description is relied upon to describe them.

In FIGS. 25 and 26 there is shown an apparatus for measuring the viscosity or flow rate of a fluid flowing therethrough comprising a matrix of constant cross-section fluid passages 69, which are rectangular in cross-section, as defined by boundary walls 67 and 68 suitably bonded, fixed, or clamped together and located within a circular pipe 62 provided for the entry and exhaust of fluid flowing through the matrix 60. The upstream edges of the separator plates 67 and the hat-sectioned spacer plates 68 have an edge contour 70 as shown in enlarged view in FIG. 27 to provide a flared inlet similar to the flared inlet 12 shown in FIG. 1, leading to each of the substantially constant cross-section portion of fluid passages 69. Two suitable pressure probes 63, which are similar to one another, are located along the length of the matrix 60 in the direction for laminar fluid flow therethrough in a manner similar to those pressure probes described with reference to FIGS. 17 to 24 and are provided for the measurement of differential pressure which is proportional to the viscosity or fluid flow rate of the fluid flowing through the matrix.

It will be further appreciated that a fluid passage matrix such as that shown in FIG. 25 and designated 60 may comprise suitably shaped plates and/or spacers so as to define fluid passages having different cross-sections to the cross-sections shown in FIG. 26, such as the fluid passages 73 having trapezoidal cross-section shown in FIG. 28 where the fluid passage defining plates have an edge contour 70 such as shown in FIG. 27 to provide the flared inlet to each of the fluid passages.

It will be appreciated that the fluid passage matrix 60 shown in FIG. 25 may comprise suitable edge profiled and formed spacers and/or plates so as to define fluid passages having two parallel opposed major boundary surface portions but with cross-sections other than those designated 69 in FIG. 26 and 73 in FIG. 28.

There is shown in FIGS. 29 and 30 a portion of a matrix of small fluid passages, such as that designated 60 in FIG. 25, comprising spacer plates 80 separated by shims 81 where such shims are located relative to the plates 80 and to each other by pins 82 so as to form thin rectangular fluid passages 83 for the laminar flow of fluid therethrough. The upstream edges of spacer plates 80 are suitably contoured and the upstream ends 84 of the shims 81 are suitably profiled as shown in FIGS. 29 and 30 so as to form a flared inlet region 85 of the fluid passage 83 in accordance with the present invention. It will be appreciated that the shims 81 need not necessarily be profiled.

In FIGS. 31 and 32 similar parts to those shown in FIGS. 29 and 30 are designated by the same reference numerals and the previous description is relied upon to describe them. In FIGS. 31 and 32, a portion of a matrix of small fluid passages is shown which has passages similar to those shown in FIGS. 29 and 30 but where the shims 81 are positioned one relative to another by means of interconnecting member 86 which may be suitably attached to or may be integral with shims 81, the integral embodiment of the interconnecting member 86 and shims 81 being shown in FIGS. 31 and 32. The shims are profiled at the inlet of the passages such that, when combined with the edge contoured spacer plates 80, the resultant passages for laminar fluid flow therethrough are in accordance with the present invention. It will be further appreciated that the interconnecting member 86 when sufficiently thin relative to the plates 80 so as not to impede the inlet flow to the passages 83, may be located upstream of the fluid flow passages as shown in FIGS. 31 and 32 or may be located downstream of the outlet from the fluid passages as shown in FIG. 37.

In FIG. 33 and 34 similar parts to those shown in FIGS. 31 and 32 are designated by the same reference numerals and the previous description is relied upon to describe them. In FIGS. 33 and 34 there are shown portions of plates 80 for forming an annular matrix of small fluid passages in contrast to the parallel location of the fluid passages shown in FIGS. 31 and 32 and where the shims 81 are integral with the spacer plates 80 in contrast with the separate shims and plates shown in FIGS. 31 and 32. The shims are contoured at the inlet of the passages to provide flared entry portions.

The spacer plates 80 shown in FIGS. 33 and 34 may be a strip member which is substantially straight in plan view or may be a segment of an annulus in plan view as shown in FIG. 33, or may be a complete annulus in plan view such that the matrix of fluid passages will have the form of a hollow cylinder when the plates 80 are stacked in layers about a common axis of symmetry.

In FIGS. 35 to 38 similar parts to those shown in FIGS. 31 and 32 are designated by the same reference numerals and the previous description is relied upon to describe them. In the embodiments shown in FIGS. 35 to 38 both the shims 81 with their integral interconnecting member 86 and the spacer plates 80 are shown as a sector of an annulus in plan view, wherein the shim portions 81 are tapered in plan view such that the rectangular fluid passage 83 formed by the shims 81 and spacer plates 83 are of substantially constant cross-section downstream of the entry portion of the passage. In FIGS. 35 and 36 there is shown apparatus having the interconnecting member 86 for shims 81 upstream of the inlet to fluid passage 83. In FIGS. 37 and 38 there is shown apparatus having the interconnecting member 86 for shims 81 downstream of the inlet to the fluid passage 83. It will be appreciated that the spacer plates and shim ring assemblies could have the shape of a complete annulus in plan view such that the matrix of fluid passages will have the form of a hollow cylinder when spacer plates 80 and shims 81 with interconnecting member 86 are stacked in layers about a common axis of symmetry.

In FIG. 39 similar parts to those shown in FIGS. 17, 18 and 19 are designated by the same reference numerals and the previous description is relied upon to describe them.

There is shown in FIG. 39 a cross-sectional side view of an apparatus similar to that shown in FIGS. 17, 18 and 19 having the substantially unobstructed inlet area 33 enclosed by an inlet cavity 47 and having the substantially unobstructed outlet area 35 enclosed by the outlet cavity 48. The top cover plate 41 and the bottom cover plate 42 carry out the same function and are located relative to shims 36, separator plates 37, by screws 38 to form a casing generally designated 49, which is similar to casing 31 described with reference to FIGS. 17, 18 and 19. The top cover plate 41, bottom cover plate 42, shims 36, screws 44, and inlet plate 45 combine to form an inlet cavity 47 with inlet port 95 connected to a source of pressurized fluid (not shown). The top cover plate 41, bottom cover plate 42, shims 36, screws 44 and outlet plate 43 combine to form an outlet cavity 48 with outlet port 46 connected to a sink for fluid inducing a flow of fluid through casing 49.

In operation pressurized fluid from a source (not shown) is supplied to the inlet port 95, flows through the inlet cavity 47 to the unobstructed inlet area 33, through the fluid passages 2 to the unobstructed outlet area 35, through the outlet cavity 48 and to the fluid sink through outlet port 46.

It will be appreciated that apparatus such as that described with reference to any of FIGS. 2, 3, 4, 17, 18, 19, 20, 21, 25, 29, 30, 31, 32, 33, 35 and 37 can have an inlet cavity 47, and an outlet cavity 48 or either an inlet cavity 47 or an outlet cavity such as that shown in FIG. 39.

Referring to FIGS. 40 to 42 there are shown graphs of test results showing the pressure drop/flow rate characteristics of fluid passages having different entries. For all of the fluid passages $b = 0.200$ inches, $h = 0.008$ inches and $L_c = 0.98$ inches. The fluid used was air.

The fluid passage for FIG. 40 has a square entry as shown in FIG. 8 and a figure of merit M of 0.729 was obtained.

The fluid passage for FIG. 41 had a radiused inlet as shown in FIG. 10 with a radius of 0.016 inches and a figure of merit M of 0.417 was obtained.

The fluid passage for FIG. 42 had a chamfered inlet as shown in FIG. 11 with a depth $d$ of 0.0694 inches and a figure of merit M of 0.584 was obtained.

For fluid passages having the rectangular cross-section of those used for the characteristics given in FIGS. 40 to 42 the figure of merit is given by $$M < 1.36 \frac{h}{d_h}$$

which is 0.707 and it will be seen that this is exceeded by the figure of merit obtained for the squared inlet of FIG. 40 while the figures of merit obtained for the appropriately profiled entries of FIGS. 41 and 42 are less than 0.707 and so fall within the scope of the present invention.

It has been found in practice that to obtain the most useful output differential pressure sensitivity for a gas such as air, the width $h$ of the constant cross-sectional area portion of the fluid is typically less than 0.02 inches and the length is preferably at least twenty five times the width $h$. However, the dimensions may be selected as required to provide adequate sensitivity for a particular application and a particular working fluid.

We claim:

1. An apparatus for measuring the flow rate and/or viscosity of a fluid comprising:
    a. a casing having a fluid passage, which is elongated in cross-section normal to the mean direction for fluid flow therein with two parallel, opposed major boundary surface portions which are parallel in a plane normal to the mean direction for fluid flow therebetween, the fluid passage comprising a flared entry portion and a portion having, in the mean direction for fluid flow therein, continuous boundary surface and a substantially constant cross-section, the flared entry portion being flared to decrease in width, without increasing in breadth, in the mean direction for fluid flow therein and forming an unobstructed flow path to the portion having, in the mean direction for fluid flow therein, a continuous boundary surface and a substantially constant cross-section, a fluid inlet to the casing and forming a substantially unobstructed flow path for fluid to the whole of an inlet area to the flared entry portion of the fluid passage, said inlet area being normal to the mean direction for flow of fluid at an inlet end of the flared entry portion, and fluid outlet from the casing and forming a substantially unobstructed flow path for fluid from the whole area of an outlet end of the fluid passage said outlet area being normal to the mean direction for flow of fluid at the outlet end of the fluid passage, and wherein
    b. the portion of the fluid passage having continuous boundary surface and a substantially constant cross-section in the mean direction for fluid flow therein has a magnitude of mean breadth which is at least as large as that given by a mean breadth to mean width ratio of 1.5 to 1, and an area in any plane normal to the mean direction for fluid flow therein which does not vary more than in the region of 2% from the mean area calculated in this manner for substantially the whole length of the said portion having continuous boundary surface and a substantially constant cross-section, and wherein
    c. the geometry of the flared entry portion of the fluid passage is such that, with laminar flow being maintained in the whole of the fluid passage, using substantially pure water at 70° F. as a standard, the flared entry portion has a "figure of merit", M which is calculated using consistent units from the relationship:

$$M = 1 - \frac{K_2 G_2}{\Delta E_2}$$

where,
$G_2$ = the mass flow rate of the substantially pure water through the fluid passage when the Reynolds number, $R_e$, is at least 2000 in the portion of the fluid passage having continuous boundary surface and a substantially constant cross-section in the mean direction for fluid flow therein, and the Reynolds number, $R_e$, in the portion of the fluid passage having continuous boundary surface and a substantially constant cross-section is defined in consistent units by the relationship:

$$R_e = \frac{h \overline{U} \rho}{\mu}, \text{ where}$$

$h$ = the width separating the parallel opposed major boundary surface portions, of the portion of the fluid passage having continuous boundary surface and a substantially constant cross-section in the mean direction for fluid flow therein, $\overline{U}$ = the mean velocity of the substantially pure water through the portion of the fluid passage having continuous boundary surface and a substantially constant cross-section in the mean direction for fluid flow therein, $\rho$ = the density of the substantially pure water, $\mu$ = the absolute viscosity of the substantially pure water, $\Delta E_2$ = a static pressure differential between the substantially pure water at or upstream of the fluid inlet to the casing and the substantially pure water within the fluid passage at a position within the portion having continuous boundary surface and a substantially constant cross-section in the mean direction for fluid flow therein and where the flow rate is $G_2$ as previously defined immediately above and which is downstream of an outlet end of the flared entry portion by at least an amount $L_e$ and is determined in consistent units by the relationship:

$L_e = 0.04 R_e h$ when the Reynolds number, $R_e$, is that where the flow rate is $G_2$ as previously defined immediately above in the portion of the fluid passage having continuous boundary surface and a substantially constant cross-section in the mean direction for fluid flow therein, $K_2$ is a constant and is defined in consistent units by $$K_2 = \frac{\Delta E_1 - \Delta E_2 \left(\frac{G_1}{G_2}\right)^2}{G_1 - \frac{(G_1)^2}{G_2}}, \text{ where}$$

$G_1$ = the mass flow rate of the substantially pure water through the fluid passage when the Reynolds number $R_e$, is less than $G_2$ and is at least 1000 in the portion of the fluid passage having continuous boundary surface and a substantially constant cross-section in the mean direction for fluid flow therein, and $\Delta E_1$ = a static pressure differential between the substantially pure water at or upstream of the fluid inlet to the casing and the substantially pure water within the fluid passage at a position within the portion having continuous boundary surface and a substantially constant cross-section in the mean direction for fluid flow therein and where the flow rate is $G_1$ as previously defined immediately above and which is downstream of the outlet end of the flared entry portion by at least an amount $L_e$ as previously defined, and where the flared entry portion "figure of merit", M, is within the limits determined by the relationship in consistent units:

$$M < 1.36 \frac{h}{d_h},$$

where $d_h$ = the hydraulic diameter of the portion of the fluid passage having continuous boundary surface and a substantially constant cross-section in the mean direction for the flow of fluid therein, and is defined in consistent units by, $$d_h = \frac{4A}{C},$$

where

A = cross-sectional area of the portion of the fluid passage having continuous boundary surface, and a substantially constant cross-section, normal to the mean direction for fluid flow therein, C = wetted perimeter of the portion of the fluid passage having continuous boundary surface and a substantially constant cross-section, in a plane normal to the mean direction for fluid flow therein, and where h is as previously defined, and d. fluid pressure detecting means in the casing for detecting a fluid pressure differential in the fluid passage, between spaced positions in the mean direction for fluid flow therein, at least one of the positions being in the portion having continuous boundary surface and a substantially cross-section, whereby e. at least one fluid characteristic to be measured, selected from the group consisting of flow rate and viscosity, is related to the pressure differential indicated by the fluid pressure detecting means and is deducible therefrom in a consistent manner for any given fluid when laminar flow is maintained in the whole of the fluid passage.

2. An apparatus according to claim 1, wherein the flared entry portion is continuously curved in the direction for fluid flow.

3. An apparatus according to claim 2, wherein the flared entry portion has a gradual and continuous increase in radius of curvature in the direction for fluid flow.

4. An apparatus according to claim 2, wherein the flared entry portion is radiused.

5. An apparatus according to claim 1, wherein the flared entry portion is chamfered.

6. An apparatus for measuring the flow rate and/or the viscous characteristics of a fluid, comprising a. a casing having a plurality of substantially identical fluid passages, which are elongated in cross-section normal to the mean direction for fluid flow therein with each passage having two parallel, opposed major boundary surface portions, which are parallel in a plane normal to the mean direction for fluid flow therethrough, each fluid passage comprising a flared entry portion and a portion having, in the mean direction for fluid flow therein, continuous boundary surface and a substantially constant cross-section, the flared entry portion of each passage being flared to decrease in width, without increasing in breadth, in the mean direction for fluid flow therein and forming an unobstructed flow path to the portion, having in the mean direction for fluid flow therein, continuous boundary surface and a substantially constant cross-section, a fluid inlet to the casing forming a substantially unobstructed flow path for fluid to the whole of an inlet area to the flared entry portion of each fluid passage, for each fluid passage said inlet area being normal to the mean direction for flow of fluid at an inlet end of the flared entry portion, a fluid outlet from the casing forming a substantially unobstructed flow path for fluid from the whole area of an outlet end of each fluid passage, for each fluid passage, said outlet area being normal to the mean direction for flow of fluid at the outlet end of that fluid passage, and wherein b. the portion of each fluid passage having continuous boundary surface and a substantially constant cross-section in the mean direction for fluid flow therein has a magnitude of mean breadth which is at least as large as that given by a mean breadth to mean width ratio of 1.5 to 1, and an area in any plane normal to the mean direction for fluid flow therein which does not vary more than in the region of 2% from the mean area calculated in this manner for the whole length of the said portion of that fluid passage having continuous boundary surface and a substantially constant cross-section, and wherein c. the geometry of the flared entry portion of each fluid passage is such that, with laminar flow being maintained in the whole of each fluid passage, using substantially pure water at 70° F. as a standard, the flared entry portion of each fluid passage has a "figure of merit", M which is substantially the same for each fluid passage and which is calculated using consistent units from the relationship:

$$M = 1 - \frac{K_2 G_2}{\Delta E_2}$$

where, $G_2$ = the mass flow rate of the substantially pure water through each of the fluid passages when the Reynolds number $R_e$, is at least 2000 in the portion of each fluid passage having continuous boundary surface and a substantially constant cross-section in the mean direction for fluid flow therein, and the Reynolds number, $R_e$, in the portion of each of the fluid passages having continuous boundary surface and a substantially constant cross-section is defined in consistent units by the relationship:

$$R_e = \frac{h \bar{U} \rho}{\mu},$$

$h$ = the width separating the parallel opposed major boundary surface portions, of the portion of each fluid passage having continuous boundary surface and a substantially constant cross-section in the mean direction for fluid flow therein, $\overline{U}$ = the mean velocity of the substantially pure water through the portion of each of the fluid passages having continuous boundary surface and a substantially constant cross-section in the mean direction for fluid flow therein, $\rho$ = the density of the substantially pure water, $\mu$ = the absolute viscosity of the substantially pure water, $\Delta E_2$ = a static pressure differential between the substantially pure water at or upstream of the fluid inlet to the casing and the substantially pure water within each fluid passage at a position within the portion having continuous boundary surface and a substantially constant cross-section in the mean direction for fluid flow therein and where the flow rate is $G_2$ as previously defined immediately above and which is downstream of an outlet end of the flared entry portion by at least an amount $L_e$ and is determined in consistent units by the relationship:

$L_e = 0.04\, R_e h$ when the Reynolds number, $R_e$, is that where the flow rate is $G_2$ as previously defined immediately above in the portion of each fluid passage having continuous boundary surface and a substantially constant cross-section in the mean direction for fluid flow therein, $K_2$ is a constant and is defined in consistent units, $$K_2 = \frac{\Delta E_1 - \Delta E_2 \left(\frac{G_1}{G_2}\right)^2}{G_1 - \frac{(G_1)^2}{G_2}},$$

where $G_1$ = the mass flow rate of the substantially pure water through each of the fluid passages when the Reynolds number $R_e$, is less than $G_2$ and is at least 1000 in the portion of each fluid passage having continuous boundary surface and a substantially constant cross-section in the mean direction for fluid flow therein, and $\Delta E_1$ = a static pressure differential between the substantially pure water at or upstream of the fluid inlet to the casing and the substantially pure water within each fluid passage at a position within the portion having continuous boundary surface and a substantially constant cross-section in the mean direction for fluid flow therein and where the flow rate is $G_1$ as previously defined immediately above and which is downstream of the outlet end of the flared entry portion by at least an amount $L_e$ as previously defined, and where the flared entry portion "figure of merit", M, is within the limits determined by the relationship in consistent units:

$$M < 1.36 \frac{h}{d_h},$$

where $d_h$ = the hydraulic diameter of the portion of each fluid passage having continuous boundary surface and a substantially constant cross-section in the mean direction for the flow of fluid therein, and is defined in consistent units by, $$d_h = \frac{4A}{C},$$

$A$ = cross-sectional area of the portion of each fluid passage having continuous boundary surface, and a substantially constant cross-section, normal to the mean direction for fluid flow therein, $C$ = wetted perimeter of the portion of each fluid passage having continuous boundary surface and a substantially constant cross-section, in a plane normal to the mean direction for fluid flow therein, and where $h$ is as previously defined, and d. fluid pressure detecting means in the casing for detecting a fluid pressure differential in at least one of the fluid passages being spaced positions in the mean direction for fluid flow therein, at least one of the positions, being in a portion of that fluid passage having continuous boundary surface and a substantially constant cross-section, whereby e. at least one fluid characteristic to be measured, selected from the group consisting of flow rate and viscosity, is related to the pressure differential indicated by the pressure detecting means and is deducible therefrom in a consistent manner for any given fluid when laminar flow is maintained in the whole of each fluid passage.

7. An apparatus according to claim 6, wherein each flared entry portion is continuously curved in the direction for fluid flow.

8. An apparatus according to claim 7, wherein each flared entry portion has a gradual and continuous increase in radius of curvature in the direction for fluid flow.

9. An apparatus according to claim 8, wherein the flared entry portion is radiused.

10. An apparatus according to claim 6, wherein the flared entry portion is chamfered.

11. An apparatus according to claim 6, wherein the flared entry portion has a double chamfer.

* * * * *